US011264132B2

(12) United States Patent
Matsui

(10) Patent No.: US 11,264,132 B2
(45) Date of Patent: Mar. 1, 2022

(54) TERMINAL DEVICE

(71) Applicant: OMRON HEALTHCARE CO., LTD., Muko (JP)

(72) Inventor: Toshinori Matsui, Muko (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 162 days.

(21) Appl. No.: 16/144,379

(22) Filed: Sep. 27, 2018

(65) Prior Publication Data

US 2019/0043608 A1    Feb. 7, 2019

Related U.S. Application Data

(63) Continuation of application No. PCT/JP2017/010117, filed on Mar. 14, 2017.

(30) Foreign Application Priority Data

Apr. 8, 2016    (JP) .............................. JP2016-077913

(51) Int. Cl.
*G16H 40/67*     (2018.01)
*G16Z 99/00*     (2019.01)
(Continued)

(52) U.S. Cl.
CPC .............. *G16H 40/67* (2018.01); *A61B 5/02* (2013.01); *G06F 16/00* (2019.01);
(Continued)

(58) Field of Classification Search
CPC ........ G16H 10/60; G16H 40/67; G06F 16/00; G06F 19/00; G06F 21/6245; G16Z 99/00; A61B 5/02; G06Q 50/22
(Continued)

(56) References Cited

U.S. PATENT DOCUMENTS 5,781,442 A * 7/1998 Engleson ............ G06F 19/3456
                                                              700/214
9,619,627 B2 * 4/2017 Holmes .............. G01N 35/0092
(Continued)

FOREIGN PATENT DOCUMENTS

CN      103997952 A    8/2014
CN      104685532 A    6/2015
(Continued)

OTHER PUBLICATIONS

Taenam Cho et al., "Vulnerabilities of android data sharing and malicious application to leaking private information," 2013 Fifth International Conference on Ubiquitous and Future Networks (ICUFN), Da Nang, 2013, pp. 37-42, doi: 10.1109/ICUFN.2013 (Year: 2013).*
(Continued)

*Primary Examiner* — Christopher L Gilligan
*Assistant Examiner* — Bennett Stephen Erickson
(74) *Attorney, Agent, or Firm* — Oliff PLC

(57) ABSTRACT

A terminal device configured to be able to communicate with a measuring device for measuring biological information includes a first processing unit executing the processing of a first application and a second processing unit executing the processing of a second application. The first processing unit stores biological information acquired from the measuring device. The second processing unit determines whether the second application is able to use biological information, based on specifying information for specifying an application able to use biological information and the identification information of the second application. When the second application is able to use biological information, the second processing unit reads out biological information from the biological information storage unit and outputs the read biological information.

9 Claims, 8 Drawing Sheets

(51) Int. Cl.
*G16H 10/60* (2018.01)
*G06F 16/00* (2019.01)
*A61B 5/02* (2006.01)
*G06F 21/62* (2013.01)

(52) U.S. Cl.
CPC ......... *G06F 21/6245* (2013.01); *G16H 10/60* (2018.01); *G16Z 99/00* (2019.02)

(58) Field of Classification Search
USPC .......................................................... 705/3
See application file for complete search history.

(56) References Cited

U.S. PATENT DOCUMENTS

| | | | |
|---|---|---|---|
| 10,561,349 B2* | 2/2020 | Wedekind | A61B 5/746 |
| 2008/0133265 A1* | 6/2008 | Silkaitis | G06F 19/3468 705/2 |
| 2010/0286488 A1* | 11/2010 | Cohen | G16H 10/65 600/300 |
| 2010/0328320 A1* | 12/2010 | Kerstna | A61N 1/37282 345/501 |
| 2013/0102853 A1* | 4/2013 | Halvorson | G16H 40/67 600/300 |
| 2014/0278535 A1* | 9/2014 | Romeo | G06Q 10/1095 705/3 |
| 2014/0367256 A1 | 12/2014 | Terashima et al. | |
| 2015/0245189 A1 | 8/2015 | Nalluri et al. | |
| 2016/0099935 A1 | 4/2016 | Luskin et al. | |
| 2016/0119434 A1 | 4/2016 | Dong et al. | |
| 2016/0210099 A1* | 7/2016 | Hampapuram | G06F 3/1423 |
| 2016/0269491 A1* | 9/2016 | Eom | H04L 67/142 |
| 2017/0116402 A1* | 4/2017 | Hirabayashi | G06F 21/31 |
| 2018/0212765 A1* | 7/2018 | Yamazaki | H04L 9/3273 |

FOREIGN PATENT DOCUMENTS

| | | |
|---|---|---|
| EP | 2799004 A1 | 11/2014 |
| JP | 2000-99458 A | 4/2000 |
| JP | 2015-121935 A | 7/2015 |
| JP | 2015-535411 A | 12/2015 |
| JP | 2016-12902 A | 1/2016 |
| JP | 2016-526207 A | 9/2016 |
| WO | 2013/099236 A1 | 7/2013 |
| WO | 2014/063121 A1 | 4/2014 |
| WO | 2016/054453 A1 | 4/2016 |

OTHER PUBLICATIONS

Mar. 3, 2021 Office Action issued in Chinese Patent Application No. 201780020466.X.

Jun. 27, 2019 Search Report issued in European Patent Application No. 17778926.0.

Jun. 6, 2017 International Search Report issued in International Patent Application No. PCT/JP2017/010117.

* cited by examiner

TERMINAL DEVICE

The present application is a continuation of International application No. PCT/JP2017/010117, filed Mar. 14, 2017, which claims priority to Japanese Patent Application No. 2016-077913, filed Apr. 8, 2016, the entire contents of each of which are incorporated herein by reference.

BACKGROUND OF THE INVENTION

Field of the Invention

The present disclosure relates to a terminal device and more specifically to a terminal device configured to be able to communicate with a measuring device for measuring biological information.

Description of the Background Art

A variety of measuring devices have been developed for measuring biological information which is various numerical information indicating the current states of human bodies, such as body temperature, blood pressure, pulse, and blood sugar level. Such biological information is private information with high security level and requires some security measures before provision.

For example, WO2013/099236 discloses a medical measuring device. This device includes a housing configured to mount thereon a biosensor in an attachable and detachable manner, the biosensor being configured to have a liquid sample of a biological object deposited thereon, a measuring component that measures biological information from the liquid sample of the biological object, a recording component that stores a result measured by the measuring component, and an information protection component that determines whether or not to prohibit a readout of personal information data stored in the recording component. In recent years, biological information measured by a variety of measuring devices is captured into terminal devices such as smartphones and displayed on the terminal devices. For example, this enables users to check biological information in various output forms by installing a variety of applications for biological information in their smartphones.

Such applications contribute to improvement of convenience for users in checking biological information, but some applications are not suitable for the use of biological information with high security level. For this reason, there is a demand for appropriately protecting biological information from such applications. WO2013/099236 discloses that a readout of private information data is prohibited when the medical measuring device is not able to perform communication with an external device, but neither teaches nor suggests techniques related to the demand as described above.

SUMMARY OF THE INVENTION

The present disclosure is made in view of the foregoing and an object in an aspect is to provide a terminal device that improves convenience for users to check biological information and protects biological information appropriately.

According to an embodiment, a terminal device configured to be able to communicate with a measuring device for measuring biological information is provided. The terminal device includes a first processing unit configured to execute processing of a first application and a second processing unit configured to execute processing of a second application. The first processing unit acquires biological information measured by the measuring device from the measuring device. The terminal device further includes a biological information storage unit configured to store biological information acquired by the first processing unit and an information storage unit configured to store specifying information for specifying an application able to use the biological information. The second processing unit determines whether the second application is able to use the biological information, at least based on identification information of the second application and the specifying information, reads out the biological information from the biological information storage unit when the second application is able to use the biological information, and outputs the read biological information.

According to another aspect, a terminal device configured to be able to communicate with a measuring device for measuring biological information is provided. The terminal device includes a first processing unit configured to execute processing of a first application and a second processing unit configured to execute processing of a second application. The first processing unit acquires biological information measured by the measuring device from the measuring device. The terminal device further includes a biological information storage unit configured to store biological information acquired by the first processing unit and an information storage unit configured to store specifying information for specifying an application able to use the biological information. The first processing unit accepts a request from the second processing unit, determines whether the second application is able to use the biological information, at least based on identification information of the second application and the specifying information, and reads out the biological information from the biological information storage unit when the second application is able to use the biological information. The second processing unit receives the biological information read out by the first processing unit and outputs the received biological information.

The present disclosure can improve convenience for users to check biological information and protects biological information appropriately.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention will be described below with reference to the figures. In the following description, the same components are denoted by the same reference signs. Their names and functions are also the same. A detailed description thereof therefore will not be repeated.

System Configuration

Figure 1:
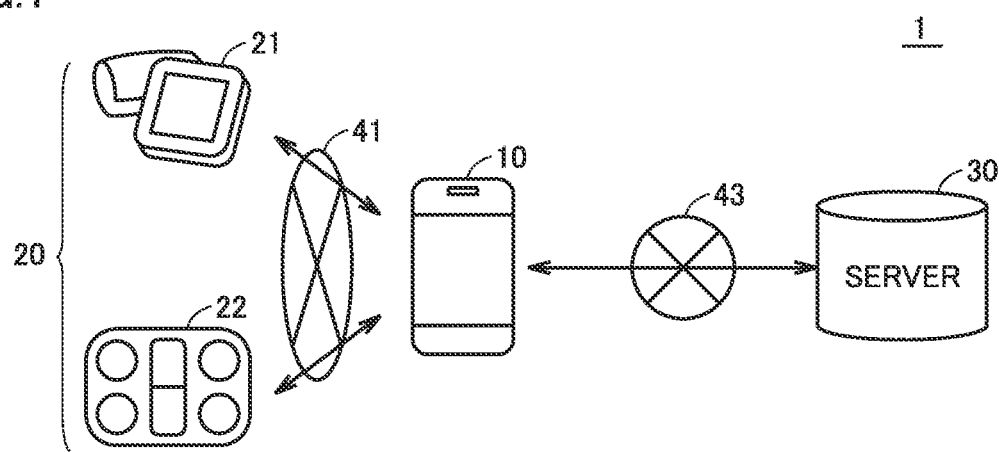
FIG. 1 is a diagram showing an overall configuration of an information processing system according to the present embodiment.

FIG. 1 is a diagram showing an overall configuration of an information processing system 1 according to the present embodiment.

Referring to FIG. 1, information processing system 1 includes a terminal device 10 as a user terminal, a sphygmomanometer 21 and a weight scale and body composition monitor 22 which are examples of the biological information measuring device for measuring biological information of users, a server device 30, and networks 41, 43.

The biological information measuring device is not limited to sphygmomanometer 21 and weight scale and body composition monitor 22 and may be any device for measuring biological information of users. For example, the biological information measuring device may be a sleep monitor or an activity tracker. For convenience of explanation, sphygmomanometer 21 and weight scale and body composition monitor 22 hereinafter may be collectively referred to as "measuring device 20".

Terminal device 10 is, for example, a smartphone having a touch panel. In the description below, a smartphone is taken as a typical example of "terminal device". However, the terminal device may be any other terminal device such as a foldable mobile phone, a tablet terminal device, a PC (personal computer), or a PDA (Personal Data Assistance).

Network 41 for connecting terminal device 10 with measuring device 20 includes a wired or wireless network. Examples of the wireless network include near field communication (USB (Universal Serial Bus) and Bluetooth (registered trademark). Network 43 for connecting terminal device 10 with server device 30 includes a variety of networks such as the Internet and mobile terminal communication networks.

In information processing system 1 according to the present embodiment, terminal device 10 acquires user's biological information measured by measuring device 20 from measuring device 20 and acquires information related to an application to be installed in terminal device 10 from server device 30. In terminal device 10, it is determined whether the installed application is able to use biological information, based on the information acquired from server device 30, and if it is determined that it is able to use, the biological information appears on a display or the like. The detail of specific processing will be described later.

Hardware Configuration (Terminal Device)

Figure 2:
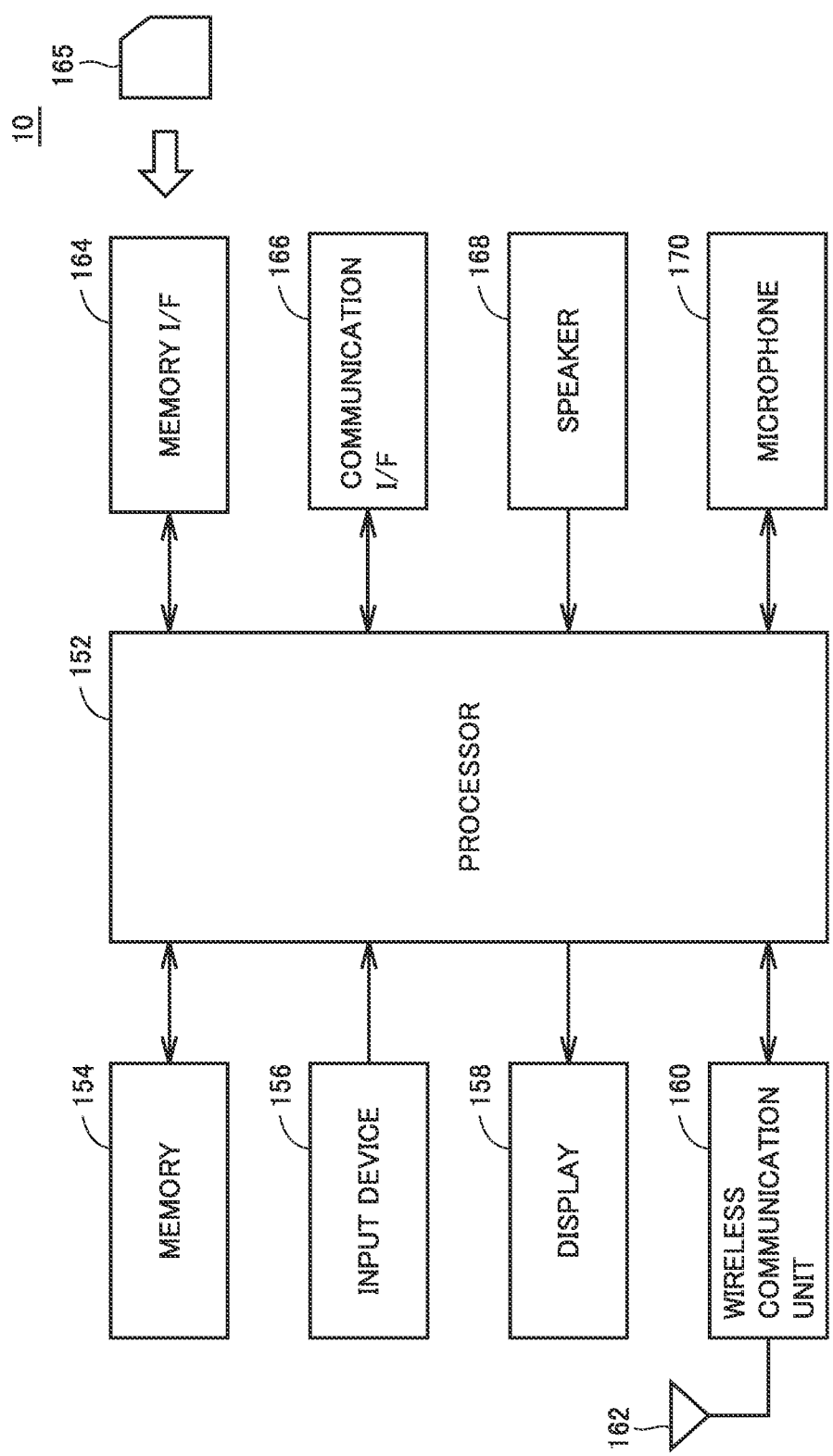
FIG. 2 is a block diagram showing an exemplary hardware configuration of a terminal device according to the present embodiment.

FIG. 2 is a block diagram showing an exemplary hardware configuration of terminal device 10 according to the present embodiment. Referring to FIG. 2, terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

Processor 152 is typically an arithmetic operation unit such as a CPU (Central Processing Unit) and an MPU (Multi Processing Unit). Processor 152 reads out and executes a program stored in memory 154 to function as a control unit that controls the operation of each unit in terminal device 10. Processor 152 implements each process (step) of terminal device 10 described later by executing the program.

Memory 154 is implemented by a RAM (Random Access Memory), a ROM (Read-Only Memory), or a flash memory. Memory 154 stores a program executed by processor 152 or data used by processor 152.

Input device 156 accepts an operation input to terminal device 10. Typically, input device 156 is implemented by a touch panel. The touch panel is provided on display 158 having the function of a display unit and is, for example, a capacitive touch panel. The touch panel detects a touch operation on the touch panel by an external object at predetermined time intervals and inputs the touch coordinates to processor 152. Input device 156 may include buttons.

Wireless communication unit 160 connects to a mobile communication network through a communication antenna 162 and transmits/receives a signal for wireless communication. This enables terminal device 10 to communicate with another communication device (for example, server device 30), for example, through a mobile communication network such as LTE (Long Term Evolution).

Memory interface 164 reads out data from an external storage medium 165. Processor 152 reads out data stored in storage medium 165 through memory interface 164 and stores the data into memory 154. Processor 152 reads out data from memory 154 and stores the data into external storage medium 165 through memory interface 164.

Storage medium 165 includes a medium for storing a program in a nonvolatile manner, such as a CD (Compact Disc), a DVD (Digital Versatile Disk), a BD (Blu-ray (registered trademark) Disc), a USB (Universal Serial Bus) memory, and an SD (Secure Digital) memory card.

Communication interface (I/F) 166 is a communication interface for exchanging a variety of data between terminal device 10 and measuring device 20 and is implemented by an adaptor or a connector. The communication scheme may be, for example, wireless communication via Bluetooth (registered trademark), a wireless LAN, and the like or may be wired communication using a USB (Universal Serial Bus) and the like.

Speaker 168 converts an audio signal applied from processor 152 into sound for output to the outside of terminal device 10. Microphone 170 accepts audio input to terminal device 10 and applies an audio signal corresponding to the audio input to processor 152.

(Server)

Server device 30 provides information processing as a whole as will be described later and may have a known hardware configuration. For example, server device 30 includes a processor for executing a variety of processing, a memory for storing a program and data, a communication interface for transmitting/receiving a variety of data to/from terminal device 10, and an input interface for accepting an instruction from a manager.

Operation Overview

Figure 3:
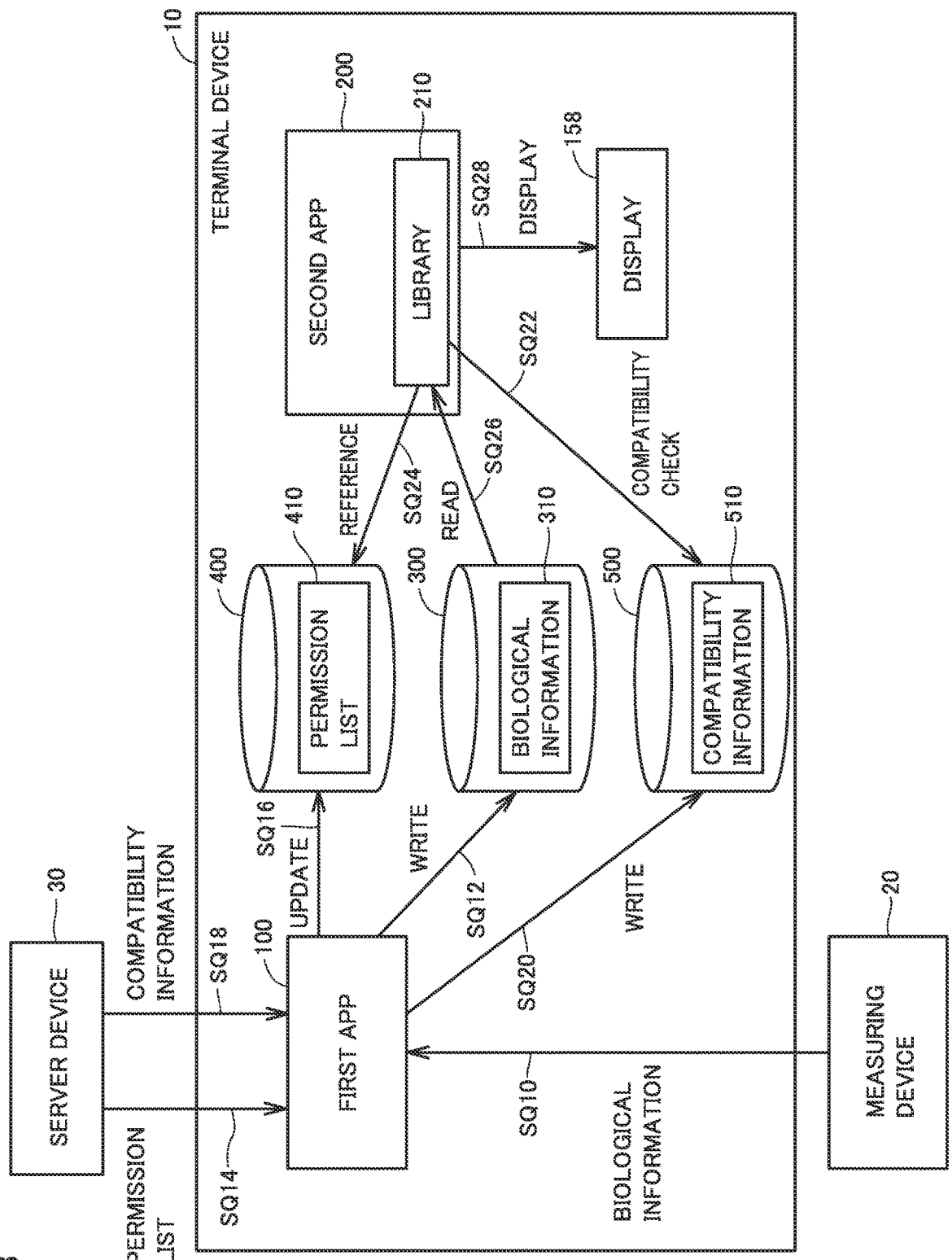
FIG. 3 is a conceptual diagram for explaining an operation overview of the information processing system according to the present embodiment.

FIG. 3 is a conceptual diagram for explaining an operation overview of information processing system 1 according to the present embodiment. Referring to FIG. 3, a first application 100 (hereinafter simply referred to as "first app 100") and a second application 200 (hereinafter simply referred to as "second app 200") are installed beforehand in terminal device 10.

First app 100 is an application prepared for collecting biological information from measuring device 20 and storing the collected biological information into terminal device 10. Second app 200 is an application capable of using biological information collected by first app 100 when a predetermined condition is satisfied.

The user therefore need to install first app 100 in terminal device 10 in order to capture biological information measured by measuring device 20 into terminal device 10. The user also installs second app 200 fitted for his/her need in terminal device 10, for example, in order to display biological information in terminal device 10 in a desired manner of display (for example, a graph of biological information). A library 210 is built in second app 200 in advance for implementing access to biological information in terminal device 10. The user may install a plurality of second apps 200 in terminal device 10.

Processor 152 of terminal device 10 executes first app 100 to execute the processing in sequences SQ10 to SQ20. Specifically, processor 152 acquires (receives) biological information from measuring device 20 (sequence SQ10) and stores the acquired biological information into biological information storage unit 300 implemented by memory 154 (sequence SQ12).

Processor 152 acquires specifying information (permission list) for specifying an application permitted to use biological information from server device 30 (sequence SQ14) and writes the acquired permission list into specifying information storage unit 400 implemented by memory 154 (sequence SQ16). Permission list 410 stored in specifying information storage unit 400 is thus updated.

Processor 152 acquires version information (compatibility information) of library 210 having compatibility with first app 100 from server device 30 (sequence SQ18) and stores the acquired compatibility information 510 into compatibility information storage unit 500 (sequence SQ20). Compatibility information 510 stored in compatibility information storage unit 500 is thus updated.

On the other hand, processor 152 executes second app 200 to read out biological information 310 stored in biological information storage unit 300 and execute the processing for outputting biological information 310 (the processing in sequences SQ22 to SQ28). Specifically, processor 152 refers to the compatibility information stored in compatibility information storage unit 500 and determines whether library 210 built in second app 200 has compatibility with first app 100 (sequence SQ22).

When library 210 has compatibility with first app 100, processor 152 refers to permission list 410 stored in specifying information storage unit 400 and determines whether second app 200 is an application able to use biological information 310 (sequence SQ24). When second app 200 is able to use biological information 310, processor 152 reads out biological information 310 (sequence SQ26). Processor 152 then displays biological information 310 (sequence SQ28).

Functional Configuration

Figure 4:
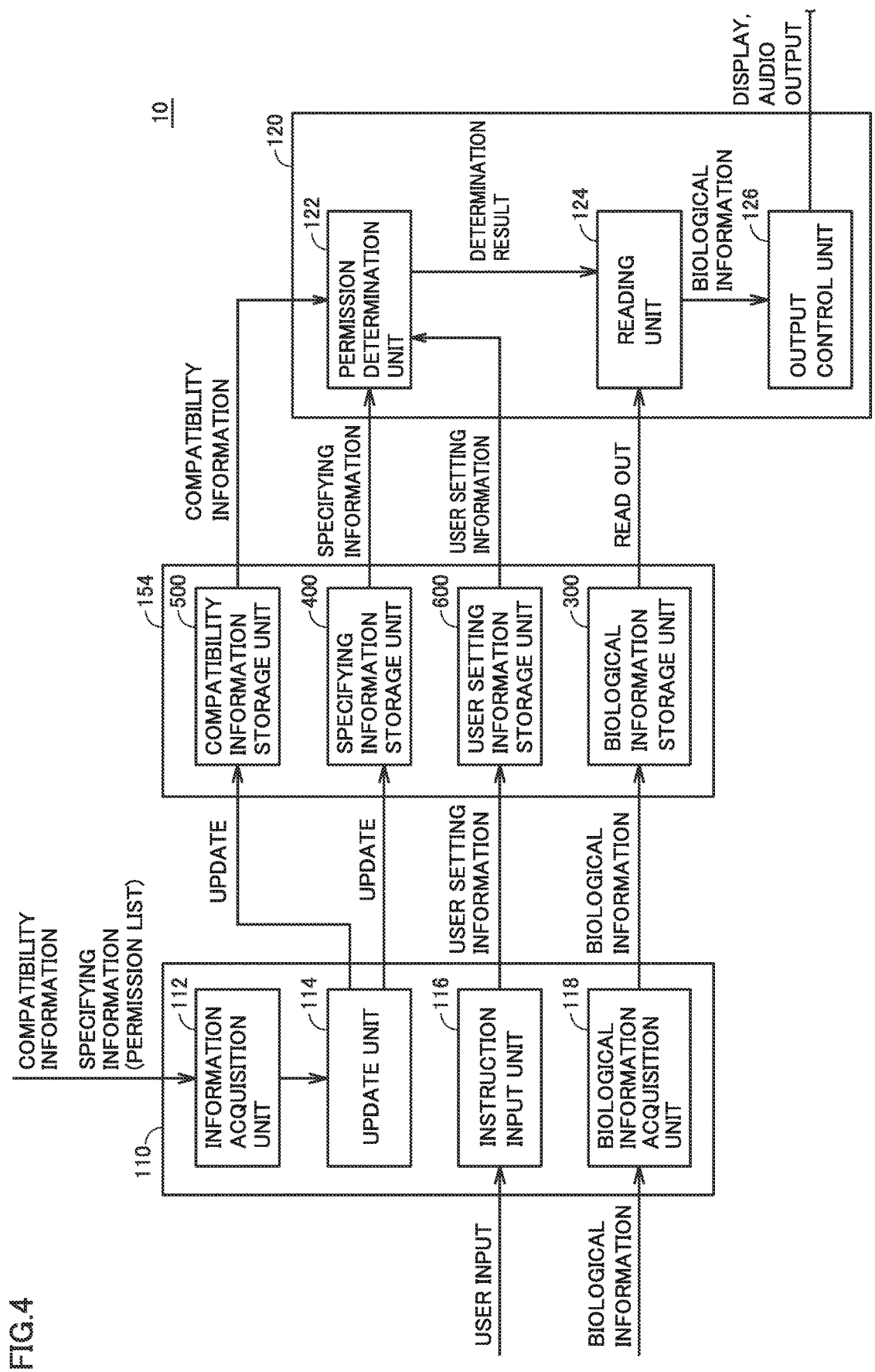
FIG. 4 is a block diagram showing a functional configuration of the terminal device according to the present embodiment.

FIG. 4 is a block diagram showing a functional configuration of terminal device 10 according to the present embodiment. Referring to FIG. 4, terminal device 10 mainly includes a first app processing unit 110, a second app processing unit 120, a biological information storage unit 300, a specifying information storage unit 400, a compatibility information storage unit 500, and a user setting information storage unit 600.

First app processing unit 110 executes processing of first app 100. Typically, first app processing unit 110 is implemented by cooperation between a computer mounted on terminal device 10 and first app 100 operated by processor 152 mounted on the computer. Specifically, first app processing unit 110 includes an information acquisition unit 112, an update unit 114, an instruction input unit 116, and a biological information acquisition unit 118.

In an aspect, information acquisition unit 112 acquires specifying information for specifying an application able to use biological information 310 stored in biological information storage unit 300. Information acquisition unit 112 accesses server device 30 to acquire the specifying information, for example, at predetermined intervals (for example, daily) or at the starting of first app 100. As used herein "able to use biological information 310" includes being able to read out biological information 310 from biological information storage unit 300 and being able to output (display, audio output) the read biological information 310. Preferably, the specifying information is a whitelist (for example, permission list 410) having identification information (app ID) of an available application.

Figure 5:
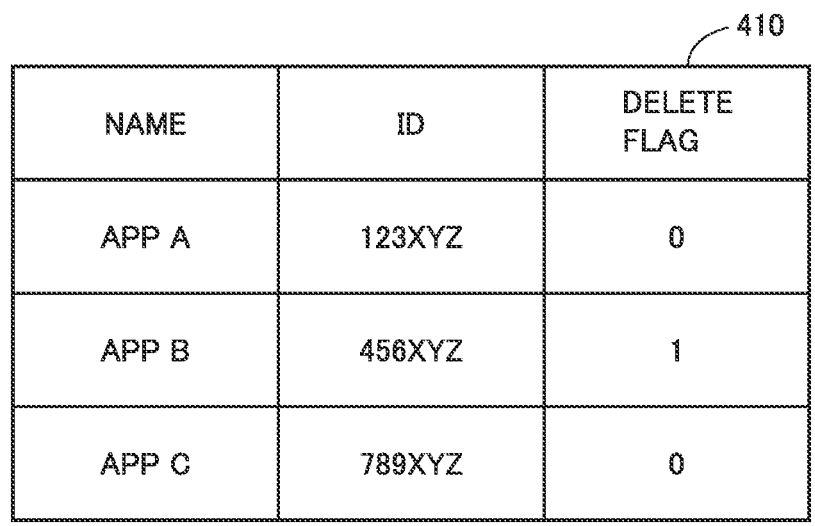
FIG. 5 is a diagram showing an exemplary permission list according to the present embodiment.

FIG. 5 is a diagram showing an exemplary permission list according to the present embodiment. Referring to FIG. 5, permission list 410 includes an application name, an app ID, and a delete flag. For example, application name "app A", app ID "123XYZ", and delete flag "0" are associated with each other. The delete flag is a flag (setting information) for temporarily setting an application corresponding to the app ID listed in permission list 410 as an application unable to use biological information 310 (prohibited application).

Specifically, delete flag "0" represents an undeleted state (available state), and delete flag "1" represents a deleted state (unavailable state). Thus, "app B" corresponding to app ID "456XYZ" listed in permission list 410 is treated as an application currently unavailable because it is associated with delete flag "1". Permission list 410 may not include an application name or a delete flag as long as it at least includes an app ID.

Referring to FIG. 4 again, in another aspect, information acquisition unit 112 acquires compatibility information 510 from server device 30 and stores the acquired compatibility information into compatibility information storage unit 500. Upon receiving, for example, a notice to update compatibility information 510 from server device 30, information acquisition unit 112 accesses server device 30 to acquire compatibility information 510. Compatibility information 510 includes version information (for example, versions "2", "3") of library 210 having compatibility with version information (for example, version "4.0") of first app 100.

In an aspect, update unit 114 updates the specifying information (for example, permission list 410) stored in specifying information storage unit 400, based on the specifying information acquired from server device 30. Specifically, update unit 114 changes old specifying information stored in specifying information storage unit 400 to new specifying information acquired from server device 30. In another aspect, update unit 114 changes old compatibility information 510 stored in compatibility information storage unit 500 to new compatibility information 510 acquired from server device 30.

Instruction input unit 116 accepts an instruction from the user through input device 156. Specifically, instruction input unit 116 accepts an instruction to permit or an instruction to prohibit second app 200 from using biological information 310. Instruction input unit 116 stores setting information in accordance with the instruction into user setting information storage unit 600.

Biological information acquisition unit 118 acquires biological information measured by measuring device 20 from measuring device 20 and stores the acquired biological information into biological information storage unit 300.

On the other hand, second app processing unit 120 executes processing of second app 200. Typically, second app processing unit 120 is implemented by cooperation between a computer mounted on terminal device 10 and second app 200 operated by processor 152 mounted on the computer. Specifically, second app processing unit 120 includes a permission determination unit 122, a reading unit 124, and an output control unit 126. Permission determination unit 122 and reading unit 124 are the functions mainly implemented by processor 152 executing library 210.

Permission determination unit 122 determines whether second app 200 is able to use biological information 310 stored in biological information storage unit 300, at least based on the identification information of second app 200 and the specifying information.

Specifically, permission determination unit 122 refers to specifying information storage unit 400 to determine whether a first condition is met. The first condition is a condition that the identification information (app ID) of second app 200 matches the app ID included in permission list 410 and second app 200 is not an unavailable application (not in a deleted state) based on the setting information (delete flag) associated with the app ID. When permission list 410 does not include a delete flag, the first condition is a condition that the app ID of second app 200 matches the app ID included in permission list 410.

Permission determination unit 122 also determines whether a second condition that library 210 has compatibility with first app 100 is met based on compatibility information 510 stored in compatibility information storage unit 500. Specifically, permission determination unit 122 determines that the second condition is met if the version information of library 210 built in second app 200 is included in the version information (compatibility information 510) of library 210 having compatibility with first app 100.

Permission determination unit 122 further determines whether a third condition that an instruction to permit second app 200 to use biological information 310 has been accepted from the user is met based on the user setting information stored in user setting information storage unit 600.

Typically, if it is determined all of the first condition, the second condition, and the third condition are met, permission determination unit 122 outputs the determination result that second app 200 is able to use biological information 310 to reading unit 124.

When the determination result that second app 200 is able to use biological information 310 is received, reading unit 124 reads out biological information 310 from biological information storage unit 300.

Output control unit 126 outputs biological information 310 read out by reading unit 124. Specifically, output control unit 126 displays biological information 310 on display 158 and/or outputs biological information 310 by sound through speaker 168.

In the configuration described above, permission determination unit 122 determines that second app 200 is able to use biological information 310 when all of the first condition, the second condition, and the third condition are met. However, embodiments are not limited to this configuration and the conditions may be changed according to a desired security level. Specifically, permission determination unit 122 may be configured to determine that second app 200 is able to use biological information 310 when the first condition is met, when the first condition and the second condition are met, or when the first condition and the third condition are met. That is, permission determination unit 122 determines that second app 200 is able to use biological information 310, based on that at least the first condition is met.

Process Procedure

Figure 6:
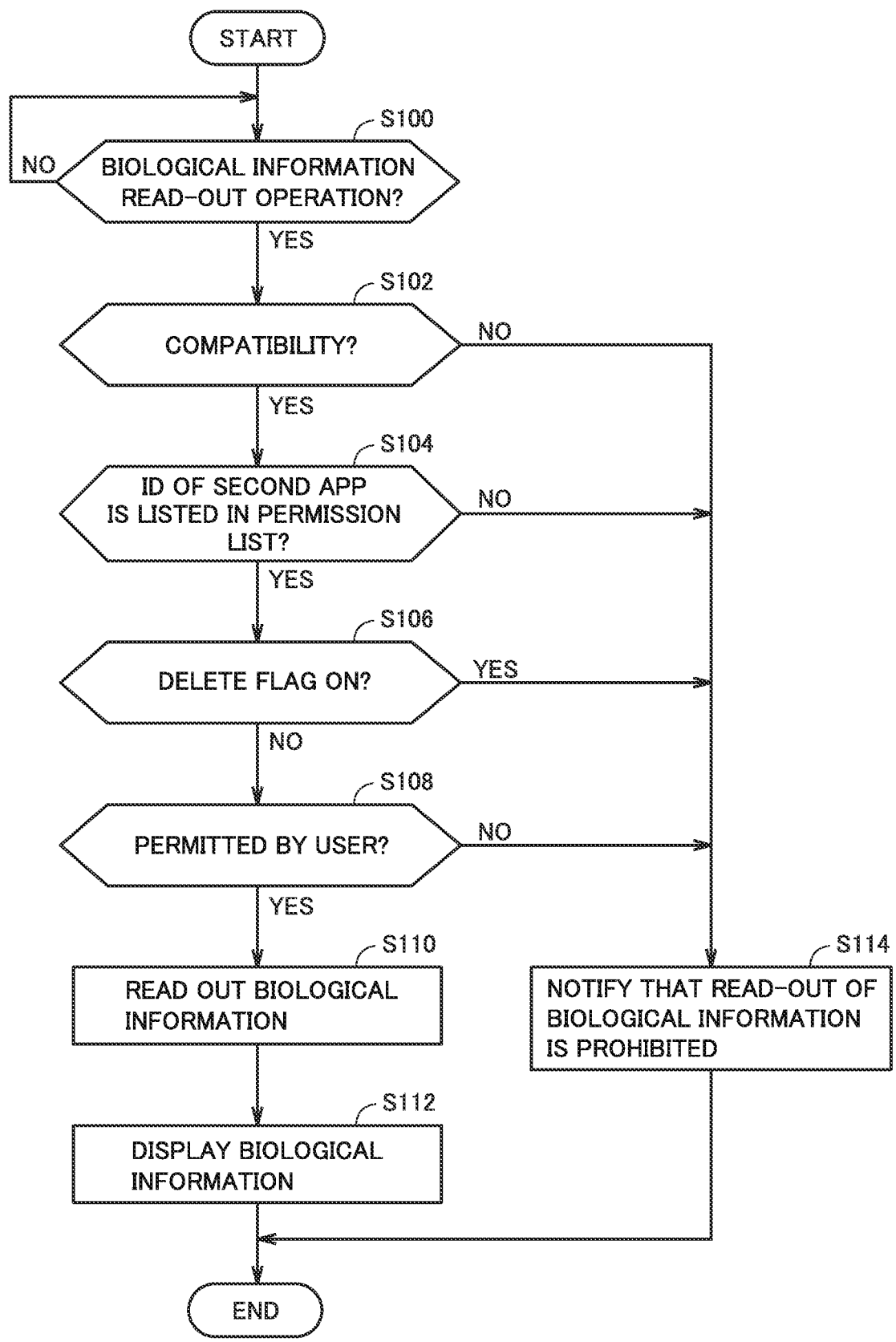
FIG. 6 is a flowchart showing an exemplary process procedure of the terminal device according to the present embodiment.

FIG. 6 is a flowchart showing an example of the process procedure of terminal device 10 according to the present embodiment. Here, the process procedure for permitting the use of biological information by second app 200 will be described. The steps below are mainly implemented by processor 152 of terminal device 10 executing a program (second app 200) stored in memory 154. It is assumed that terminal device 10 has acquired a variety of information (biological information, permission list 410, compatibility information) from measuring device 20 and server device 30.

Referring to FIG. 6, processor 152 starts second app 200 to determine whether an operation to read out biological information 310 by the user has been accepted through input device 156 (step S100). When the operation has not been performed (NO in step S100), processor 152 repeats the processing in step S100. When the operation has been performed (YES in step S100), it is determined whether library 210 has compatibility with first app 100, based on the compatibility information stored in memory 154 (step S102).

When it does not have the compatibility (NO in step S102), processor 152 gives a notice (for example, displayed on display 158) that second app 200 is an application prohibited to read out biological information 310 (step S114), and terminates the processing. When it has the compatibility (YES in step S102), processor 152 determines whether the app ID of second app 200 is listed in permission list 410 stored in memory 154 (step S104).

When the app ID is not listed (NO in step S104), processor 152 executes the processing in step S114 and terminates the processing. When the app ID is listed (YES in step S104), processor 152 determines whether the delete flag associated with the app ID is ON (deleted state) (step S106).

When the delete flag is ON (YES in step S106), processor 152 executes the processing in step S114 and terminates the processing. When the delete flag is OFF (NO in step S106), processor 152 determines whether an instruction to permit second app 200 to use biological information 310 has been accepted from the user (whether permission setting is made by the user), based on the user setting information stored in memory 154 (step S108).

When the instruction to permit has not been accepted (NO in step S108), processor 152 executes the processing in step S114 and terminates the processing. When the instruction to permit has been accepted (YES in step S108), processor 152 reads out biological information 310 stored in memory 154

(step S110). Processor 152 then displays biological information 310 on display 158 (step S112) and terminates the processing.

Modification

In the foregoing embodiment, the function (corresponding to permission determination unit 122 in FIG. 4) of determining whether second app 200 is able to use biological information 310 and the function (corresponding to reading unit 124 in FIG. 4) of reading out biological information 310 from biological information storage unit 300 are provided on the second app 200 side. However, embodiments are not limited this configuration. In a modification of the present embodiment, the functions equivalent to permission determination unit 122 and reading unit 124 are provided on the first app 100 side.

Figure 7:
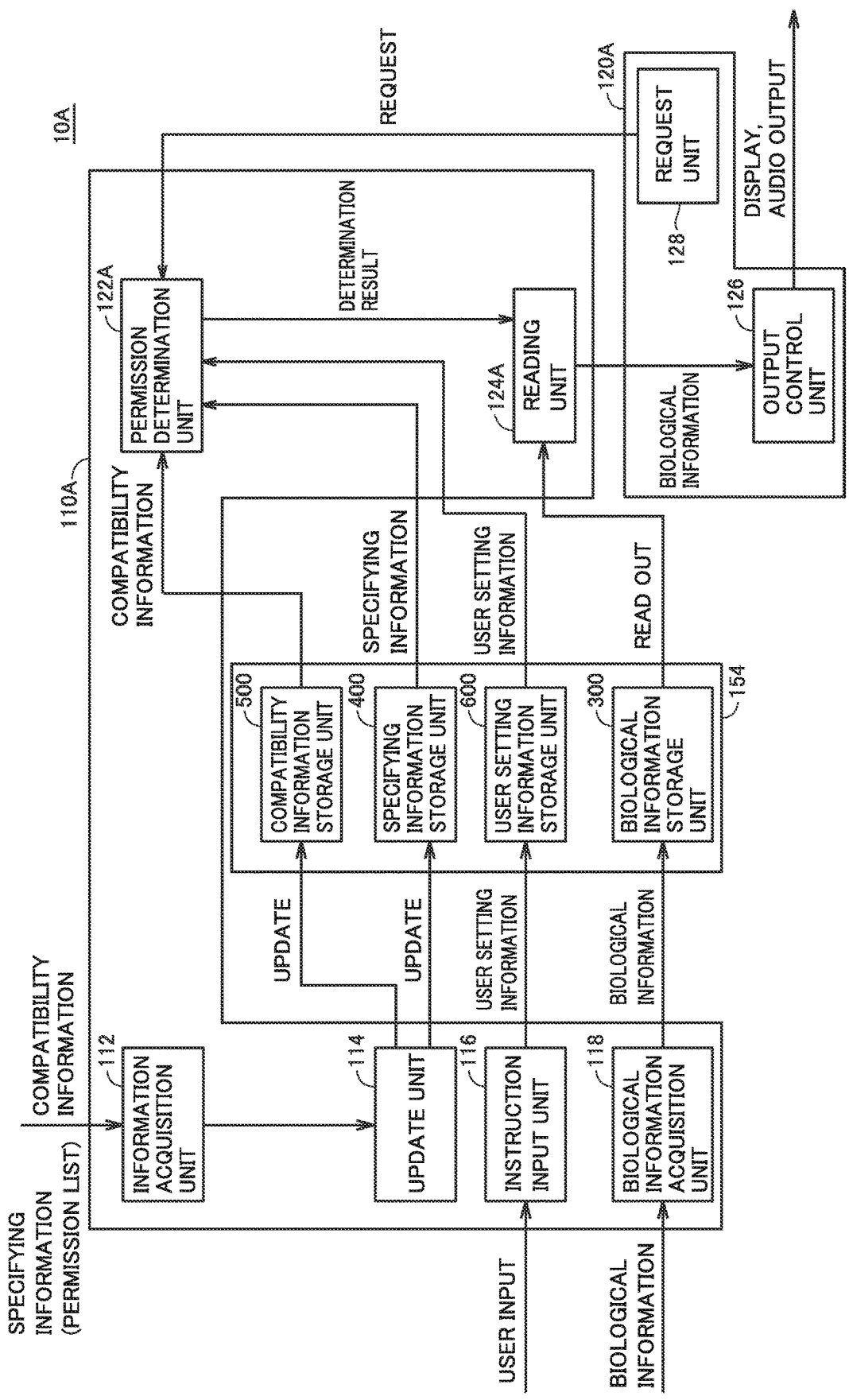
FIG. 7 is a block diagram showing a functional configuration of a terminal device according to a modification of the present embodiment.

FIG. 7 is a block diagram showing a functional configuration of a terminal device 10A according to a modification of the present embodiment. Referring to FIG. 7, terminal device 10A is a configuration in which first app processing unit 110 is replaced by a first app processing unit 110A and second app processing unit 120 is replaced by a second app processing unit 120A in the configuration of terminal device 10 in FIG. 4.

Specifically, first app processing unit 110A is configured such that a permission determination unit 122A and a reading unit 124A are added to first app processing unit 110. Second app processing unit 120A is configured such that permission determination unit 122 and reading unit 124 are deleted from second app processing unit 120 and a request unit 128 is newly added. A configuration different from terminal device 10 in the configuration of terminal device 10A will be described, and a detailed description of a similar configuration will not be repeated.

Request unit 128 included in second app processing unit 120A makes a permission request for reading out biological information 310 stored in biological information storage unit 300 to first app 100. This request includes the identification information of second app 200 and the version information of library 210.

Upon accepting the permission request, permission determination unit 122A included in first app processing unit 110A executes the determination processing similar to permission determination unit 122 described above, using the identification information of second app 200 and the version information of library 210.

Specifically, permission determination unit 122A determines whether second app 200 is an application that is able to use biological information 310 by determining whether the first condition, the second condition, and the third condition are met. Permission determination unit 122A outputs the determination result to reading unit 124A included in first app processing unit 110A. Specifically, permission determination unit 122A permits reading unit 124A to read out biological information 310 if it is determined that second app 200 is able to use biological information 310.

When receiving the permission, reading unit 124A reads out biological information 310 from biological information storage unit 300 and transmits biological information 310 to second app processing unit 120A (output control unit 126). Output control unit 126 then receives biological information 310 read out by first app processing unit 110A (reading unit 124A) and outputs the received biological information 310.

Advantages

According to the present embodiment, when a predetermined condition is met, biological information acquired on the first app 100 side is available on the second app 200 side, so that the user can grasp biological information in various points of view by installing a variety of second apps 200. Setting the conditions described above can prevent a malicious second app 200 from abusing biological information, thereby improving security.

According to the present embodiment, the security during use of biological information can be further improved by checking the compatibility between first app 100 and library 210 built in second app 200 and checking whether the permission setting by the user is made. In addition, the security level can be changed if necessary by setting whether to add the second condition and the third condition, other than the first condition.

Other Embodiments (1) In the foregoing embodiment, permission list 410 may further include information (type information) indicating the type of biological information 310 that second app 200 is able to use, in addition to the app ID and the delete flag.

Figure 8:
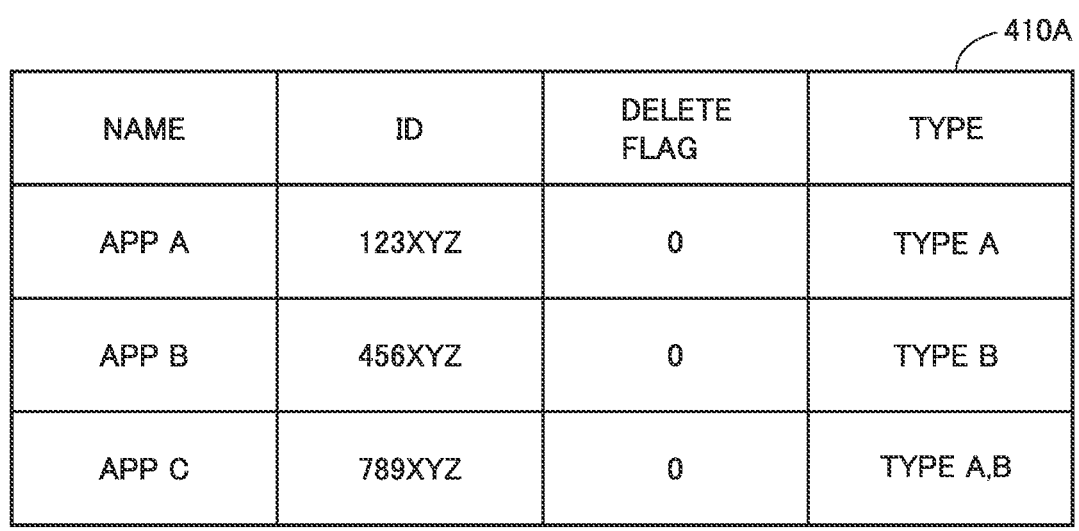
FIG. 8 is a diagram showing an exemplary permission list according to another embodiment.

FIG. 8 is a diagram showing an exemplary permission list according to another embodiment. For simplification of explanation, all of the delete flags are set to "0" (undeleted state). Referring to FIG. 8, permission list 410A additionally includes the item (type information) indicating the type of biological information in permission list 410 shown in FIG. 5. Specifically, "app A" is associated with type A (for example, blood pressure), "app B" is associated with type B (for example, weight and body composition), and "app C" is associated with types A and B.

For example, when second app 200 is "app A", second app processing unit 120 can read out blood pressure information stored in biological information storage unit 300 but cannot read out weight and body composition information. When second app 200 is "app C", second app processing unit 120 can read out blood pressure information and weight and body composition information stored in biological information storage unit 300. That is, when second app 200 is able to use biological information 310, second app processing unit 120 can read out, of the biological information 310, biological information of the type indicated by the type information. This configuration can limit biological information that the second app 200 is allowed to use, according to the type.

(2) In the foregoing embodiments, second app 200 may instruct first app 100 to acquire biological information, and in response to the instruction, first app 100 may acquire biological information from measuring device 20.

For example, the user gives an instruction to acquire biological information that the user wishes to use in second app 200 from measuring device 20, during the starting of second app 200. Second app processing unit 120 accepts the instruction through input device 156 and then requests first app processing unit 110 to acquire biological information from measuring device 20 in accordance with the instruction (an acquisition request is output to first app processing unit 110). First app processing unit 110 accepts the acquisition request and then accesses measuring device 20 to acquire biological information and store the acquired biological information into biological information storage unit 300.

First app processing unit 110 may determine whether to meet the acquisition request based on permission list 410. Specifically, if the app ID of second app 200 included in the acquisition request received from second app processing unit 120 is included in permission list 410, first app processing unit 110 acquires biological information from measuring device 20 in accordance with the acquisition request. On the other hand, if the app ID of second app 200 is not included in permission list 410, first app processing unit 110 notifies second app processing unit 120 that the acquisition request is not to be accepted.

The user thus can indirectly give an instruction to first app 100 using second app 200. This saves the time and effort of starting first app 100 to acquire biological information. Since first app 100 does not accept an acquisition request from a second app 200 of which security is not guaranteed, unnecessary processing is not executed and the load on terminal device 10 is not increased.

(3) In the foregoing embodiment, the specifying information is a whitelist. This configuration can improve security compared with a blacklist. However, for example, when security is sufficiently guaranteed by adding the second condition (checking the compatibility) and the third condition (checking the permission setting by the user), the specifying information may be a blacklist (prohibition list). When the specifying information is a prohibition list, the first condition is a condition that the identification information of second app 200 is not listed in the prohibition list.

(4) In the foregoing embodiment, a program may be provided that allows a computer to function to execute the control illustrated in the flowchart described above. Such a program may be recorded on a non-transitory computer-readable recording medium accompanying the computer, such as a flexible disk, a CD (Compact Disk Read Only Memory), a secondary storage device, a main storage device, and a memory card and provided as a program product. Alternatively, the program may be recorded on a recording medium contained in the computer, such as a hard disk. Alternatively, the program may be downloaded via a network.

The program may invoke necessary modules, of program modules provided as part of the operating system (OS) of the computer, in a predetermined sequence and at a predetermined timing to execute the processing. In this case, the program itself does not include the modules but may cooperate with the OS to execute the processing. The program according to the present embodiment may embrace such a program that does not include modules.

The program according to the present embodiment may be built in another program. Also in this case, the program itself does not include modules included in another program and cooperates with another program to execute the processing. The program according to the present embodiment may embrace such a program built in another program.

(5) The configuration illustrated as the foregoing embodiment is an example of the configuration of the present invention and may be combined with other known techniques or may be modified, for example, partially omitted without departing from the spirit of the present invention. In the foregoing embodiments, the processing or configuration described in other embodiments may be applied as appropriate and carried out.

Supplementary Notes

According to an embodiment, a terminal device configured to be able to communicate with a measuring device for measuring biological information is provided. The terminal device includes a first processing unit configured to execute processing of a first application and a second processing unit configured to execute processing of a second application. The first processing unit acquires biological information measured by the measuring device from the measuring device. The terminal device further includes a biological information storage unit configured to store biological information acquired by the first processing unit and an information storage unit configured to store specifying information for specifying an application able to use the biological information. The second processing unit determines whether the second application is able to use the biological information, at least based on identification information of the second application and the specifying information, reads out the biological information from the biological information storage unit when the second application is able to use the biological information, and outputs the read biological information.

Preferably, the first processing unit updates the specifying information stored in the information storage unit, based on the specifying information acquired from an external device.

Preferably, the specifying information is a whitelist having identification information of the application able to use.

Preferably, the whitelist further has setting information for temporarily setting an application listed in the whitelist as an application unable to use the biological information. The second processing unit reads out the biological information from the biological information storage unit when identification information of the second application matches identification information of an application listed in the whitelist and it is determined that the second application is not the application unable to use, based on the setting information.

Preferably, the second processing unit reads out the biological information from the biological information storage unit when identification information of the second application matches identification information of the application able to use and an instruction to permit the second application to use the biological information is accepted from a user.

Preferably, the whitelist further includes type information indicating a type of the biological information that the second application is able to use. When the second application is able to use biological information stored in the biological information storage unit, the second processing unit reads out, of the biological information, biological information of a type indicated by the type information.

Preferably, the second processing unit requests the first processing unit to acquire biological information measured by the measuring device from the measuring device. When accepting the request, the first processing unit acquires the biological information from the measuring device.

According to another aspect, a terminal device configured to be able to communicate with a measuring device for measuring biological information is provided. The terminal device includes a first processing unit configured to execute processing of a first application and a second processing unit configured to execute processing of a second application. The first processing unit acquires biological information measured by the measuring device from the measuring device. The terminal device further includes a biological information storage unit configured to store biological information acquired by the first processing unit and an information storage unit configured to store specifying information for specifying an application able to use the biological information. The first processing unit accepts a request from the second processing unit, determines whether the second application is able to use the biological information, at least based on identification information of the second application and the specifying information, and reads out the biological information from the biological information storage unit when the second application is able to use the biological information. The second processing unit receives the biological information read out by the first processing unit and outputs the received biological information.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A terminal device configured to be able to communicate with a measuring device for measuring biological information, the terminal device comprising:
a processor configured to function as:
a first processing unit configured to execute processing of a first application, the first processing unit acquiring, from the measuring device, biological information measured by the measuring device; and
a second processing unit configured to execute processing of a second application;
a biological information storage unit comprising a memory and configured to store biological information acquired by the first processing unit; and
an information storage unit comprising a memory and configured to store specifying information for specifying an application able to use the biological information,
wherein the second processing unit is configured to:
determine whether the second application is able to use the biological information by performing an authentication process without the biological information, at least based on identification information of the second application and the specifying information, the identification information of the second application represented by a stored character string corresponding to the second application, and
when the second processing unit determines that the second application is able to use the biological information, read out the biological information from the biological information storage unit and subsequently output the read biological information to a display.

2. The terminal device according to claim 1, wherein the first processing unit is configured to update the specifying information stored in the information storage unit, based on the specifying information acquired from an external device.

3. The terminal device according to claim 1, wherein the specifying information is a whitelist having identification information of the application able to use.

4. The terminal device according to claim 1, wherein the second processing unit is configured to read out the biological information from the biological information storage unit when identification information of the second application matches identification information of the application able to use and an instruction to permit the second application to use the biological information is accepted from a user.

5. The terminal device according to claim 1, wherein
the second processing unit is configured to request the first processing unit to acquire biological information measured by the measuring device from the measuring device, and
when accepting the request, the first processing unit is configured to acquire the biological information from the measuring device.

6. The terminal device according to claim 1, wherein the second processing unit is configured to determine whether the second application is able to use the biological information based on a determination as to whether the second application is compatible with the first application by determining if version information of a library built in the second application is has compatibility with the first application.

7. The terminal device according to claim 3, wherein
the whitelist further has setting information for temporarily setting an application listed in the whitelist as an application unable to use the biological information, and
the second processing unit is configured to read out the biological information from the biological information storage unit when identification information of the second application matches identification information of an application listed in the whitelist and it is determined that the second application is not the application unable to use, based on the setting information.

8. The terminal device according to claim 3, wherein
the whitelist further includes type information indicating a type of the biological information that the second application is able to use, and
when the second application is able to use biological information stored in the biological information storage unit, the second processing unit is configured to read out, of the biological information, biological information of a type indicated by the type information.

9. A terminal device configured to be able to communicate with a measuring device for measuring biological information, the terminal device comprising:
a processor configured to function as:
a first processing unit configured to execute processing of a first application, the first processing unit acquiring, from the measuring device, biological information measured by the measuring device; and
a second processing unit configured to execute processing of a second application;
a biological information storage unit comprising a memory and configured to store biological information acquired by the first processing unit; and
an information storage unit comprising a memory and configured to store specifying information for specifying an application able to use the biological information,
wherein the first processing unit is configured to:
accept a request from the second processing unit and determine whether the second application is able to use the biological information by performing an authentication process without the biological information, at least based on identification information of the second application and the specifying information, the identification information of the second application represented by a stored character string corresponding to the second application, and
when the first processing unit determines that the second application is able to use the biological information, read out the biological information from the biological information storage unit, and
wherein the second processing unit is configured to receive the biological information read out by the first processing unit and to output the received biological information to a display.

* * * * *